United States Patent
Ding et al.

(12)

(10) Patent No.: US 6,309,723 B1
(45) Date of Patent: Oct. 30, 2001

(54) BIOMATERIALS WITH HYDROPHILIC SURFACES

(75) Inventors: Samuel Ding, Vernon Hills; Chuan Qin, Grayslake; Barrett Rabinow, Skokie, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/701,195

(22) Filed: Aug. 21, 1996

Related U.S. Application Data

(63) Continuation of application No. 08/284,749, filed on Aug. 2, 1994, now abandoned, which is a continuation of application No. 07/921,174, filed on Jul. 29, 1992, now abandoned.

(51) Int. Cl.$^7$ .............................. B29D 7/01; B29D 22/00
(52) U.S. Cl. ................... 428/36.92; 428/35.7; 428/36.7; 428/319.3; 428/319.7; 428/319.9
(58) Field of Search ............................ 428/36.7, 500, 428/36.92, 35.7, 319.3, 319.7

(56) References Cited

U.S. PATENT DOCUMENTS

| | | | |
|---|---|---|---|
| 2,988,282 | * 6/1961 | Guandrique et al. | 264/13 |
| 2,988,782 | * 6/1961 | Guandique et al. | 264/13 |
| 3,222,314 | 12/1965 | Wolinski | 260/33.2 |
| 3,329,557 | 7/1967 | Magat et al. | 161/172 |
| 3,355,413 | 11/1967 | Kiefer | 260/31.4 |
| 3,410,927 | 11/1968 | Crovatt, Jr. | 260/860 |
| 3,425,981 | 2/1969 | Puletti et al. | 260/41 |
| 3,426,107 | 2/1969 | Scruggs et al. | 260/897 |
| 3,524,905 | 8/1970 | Coates | 260/897 |
| 3,549,727 | 12/1970 | Coates et al. | 260/897 |
| 3,645,939 | 2/1972 | Gaylord | 260/17.4 |
| 3,682,846 | 8/1972 | Keizo Sano et al. | 260/2.5 |
| 3,789,085 | 1/1974 | Kishimoto et al. | 260/897 |
| 3,882,259 | * 5/1975 | Nohara et al. | 428/36.7 |
| 3,940,469 | 2/1976 | Steigelmann et al. | 264/177 |
| 4,048,131 | 9/1977 | Keske et al. | 260/33.2 |
| 4,129,717 | 12/1978 | Praetorius et al. | 528/421 |
| 4,159,975 | 7/1979 | Praetorius et al. | 525/91 |
| 4,228,250 | 10/1980 | Pritchett | 525/57 |
| 4,239,826 | * 12/1980 | Knott, II et al. | 428/36.7 |
| 4,254,169 | * 3/1981 | Schroeder | 428/36.7 |
| 4,284,671 | 8/1981 | Cancio et al. | 428/35 |
| 4,327,009 | 4/1982 | Allen et al. | 524/114 |
| 4,337,188 | 6/1982 | Climenhage et al. | 524/140 |
| 4,358,550 | * 11/1982 | Jacono et al. | 264/142 |
| 4,362,844 | 12/1982 | Lemstra et al. | 525/57 |
| 4,412,025 | 10/1983 | Corwin et al. | 524/241 |
| 4,415,691 | 11/1983 | Allen et al. | 524/114 |
| 4,464,438 | 8/1984 | Lu | 428/516 |
| 4,474,928 | 10/1984 | Hoenig et al. | 525/186 |
| 4,500,677 | 2/1985 | Maruhashi et al. | 525/57 |
| 4,522,967 | 6/1985 | Sheldon et al. | 524/377 |
| 4,532,187 | 7/1985 | Hoenig et al. | 428/457 |
| 4,547,530 | 10/1985 | McCreedy et al. | 521/139 |
| 4,576,721 | 3/1986 | McCreedy et al. | 210/640 |
| 4,600,404 | 7/1986 | Sheldon et al. | 604/387 |
| 4,600,746 | 7/1986 | Schmukler et al. | 525/57 |
| 4,675,361 | 6/1987 | Ward, Jr. | 525/92 |
| 4,678,833 | 7/1987 | McCreedy et al. | 525/66 |
| 4,686,137 | 8/1987 | Ward, Jr. et al. | 428/290 |
| 4,693,887 | * 9/1987 | Shah | 424/486 |
| 4,771,089 | 9/1988 | Ofstead | 524/41 |
| 4,781,714 | * 11/1988 | Eckenhoff et al. | 424/422 |
| 4,786,685 | 11/1988 | Takida et al. | 525/58 |
| 4,803,035 | * 2/1989 | Kresge et al. | 264/142 |
| 4,861,830 | 8/1989 | Ward, Jr. | 525/92 |
| 4,883,699 | * 11/1989 | Aniuk et al. | 428/36.9 |
| 4,920,158 | 4/1990 | Murray et al. | 523/111 |
| 4,994,267 | * 2/1991 | Jobbotsky et al. | 424/486 |
| 5,010,139 | 4/1991 | Yu | 525/187 |
| 5,013,769 | 5/1991 | Murray et al. | 523/111 |
| 5,023,036 | 6/1991 | Lee et al. | 264/211 |
| 5,032,434 | 7/1991 | Sanchez et al. | 428/36.7 |
| 5,045,594 | 9/1991 | Samuel et al. | 525/57 |
| 5,132,149 | * 7/1992 | Kotani et al. | 428/36.7 |
| 5,582,820 | * 12/1996 | Yamamoto et al. | 428/36.7 |

FOREIGN PATENT DOCUMENTS

| | | | |
|---|---|---|---|
| 143213 | * 4/1979 | (DE) | 264/142 |
| 887353 | 1/1962 | (GB) . | |
| 52023149 | 2/1977 | (JP) . | |
| 5420994 | * 7/1979 | (JP) | 428/36.7 |
| 62169052 | 7/1987 | (JP) . | |
| 1288408 | * 11/1989 | (JP) | 268/142 |

* cited by examiner

*Primary Examiner*—Thurman K. Page
(74) *Attorney, Agent, or Firm*—Mark J. Buonaiuto; Joseph A. Fuchs

(57) ABSTRACT

A protein-compatible polymer blend made from a water-soluble polymer and a matrix polymer. The glass transition temperature of either the water-soluble polymer or the matrix polymer is greater than the application temperature, i.e., the temperature at which the protein-compatible polymer blend is being used.

45 Claims, No Drawings

BIOMATERIALS WITH HYDROPHILIC SURFACES

This is a continuation of application Ser. No. 08/284,749, filed on Aug. 2, 1994, now abandoned, which is a continuation of application Ser. No. 07/921,174, filed on Jul. 29, 1992, now abandoned.

TECHNICAL FIELD

The invention relates generally to polymer blends having improved surface characteristics. In particular, the invention relates to a polymer blend which can be extruded into films or otherwise processed into other materials. The processed polymer blend shows a markedly decreased tendency to adsorb protein from protein-containing solutions.

BACKGROUND OF THE INVENTION

Adsorption of solutions onto the materials of containers that are used to store and transport drugs has been well documented. For example, reductions in the potency of digitoxin, insulin, mithramycin and vincristine sulfate have been noted upon passage of these drugs through in-line intravenous filters containing man-made materials, such as cellulose ester membranes.

Protein is adsorbed by most such man-made materials, including liquid containers made of various polymers, such as cellulose esters. For example, protein adsorption is a concern for wearers of plastic contact lenses. Protein from the tears of contact lens wearers can be adsorbed onto the contact lens surface. The protein can dry and, in the process, distort the smooth surface of that lens, clouding the vision of the wearer.

Polymeric liquid containers, tubing and filters are used to contain, transport and filter protein-containing solutions, such as blood, and solutions containing the proteins like albumin, porcine insulin, human chronic gonadotrophin (HCG), bovine serum albumin, and sheep immunoglobulin G (IgG). Some of these proteins are adsorbed into the artificial polymeric surface, resulting in a lowering of the protein content in that solution. In some applications, this protein adsorption is not a concern, as the protein content is not critical. To compensate for protein adsorption in such instances, an excess of protein is placed in many of these protein-containing solutions. In this way, protein can be adsorbed out of these prior protein-containing solutions without compromising the quality or efficacy of those solutions.

In instances where the quantity of protein administered to a patient is important and where that protein is administered by solution to that patient, the amount of protein administered can be determined indirectly by a process called patient "titration." For example, the actual amount of insulin received by a diabetic patient can be determined by measuring the blood glucose level of that patient after administration of the theoretically correct insulin dosage. If the blood glucose level after administration is still unacceptably high, then the medical professional would infer that a part of the theoretically correct insulin dosage has been lost, prior to ingestion by the patient, to polymeric storage, transport or filtration units. To compensate for this loss, an additional amount of insulin necessary to attain the desired blood glucose level can then be determined and administered. This method of compensation for inaccurately administered drug dosages has been accepted because a biological endpoint is readily determined and the drug is relatively inexpensive.

Some prior art solutions, however, including blood or protein drug solutions, can be adversely affected by protein adsorption onto artificial surfaces. For example, protein adsorption from blood may induce thrombus, i.e., vessel-clogging blood clot, in the patient receiving the blood. Denaturation, a process described below, may occur in a protein drug solution.

In addition, certain newly-created genetically engineered "bio-tech" drugs are especially sensitive. Novel plant- or animal-based bio-tech drugs on the market or being developed include colony stimulating factors, growth factors and hormones, interferons, interleukins, and monoclonal antibodies. Because of the biological specificity of these agents, they are effective even when administered in amounts much smaller than those of many more conventional drugs. It is this smaller dose size that renders these drugs more susceptible to adsorptive protein losses. The amount of protein in these bio-tech drugs is measured in parts per million (ppm), rather than in weight or volume percentages. Conventional containers are unsuitable for these new bio-tech drugs, as even minuscule protein adsorption onto those containers can reduce their level of protein to a point where those drugs are unusable. Moreover, even if the protein is not permanently adsorbed onto the polymeric container, protein molecules can be adsorbed onto the container and then released. This adsorption and release can change the shape of the molecule, a process known as denaturation. When protein molecules in a bio-tech drug or protein drug solution have undergone denaturation, there is a significant risk that they will lose their efficacy and utility.

Because bio-tech drugs can cost several thousand dollars per dose, it is imperative that neither the small amount of protein nor the nature of the protein in those solutions be changed. Moreover, the regulatory agency approvals of this class of susceptible drugs increase rapidly with each passing year.

One method of inhibiting protein loss from protein-containing solutions is the addition of poly(ethylene oxide)-containing surfactants to protein solutions. The addition of poly(ethylene oxide) stabilizes these aqueous proteins. It would be preferable, however, to store protein solutions in containers which do not adsorb proteins, rather than add surfactants to the solutions. The addition of any surfactant in the protein solution will result in the administration of the surfactant to the patient, allowing for the possibility of an adverse reaction.

In attempts to achieve this objective, a protein-compatible material containing the water-soluble polymer poly(ethylene oxide) (PEO) has been manufactured by the present inventors. In the present context, the term "protein-compatible" shall mean a material which (a) absorbs lower amounts of protein than conventional polymeric materials when placed in contact with protein-containing solutions; and (b) lowers the potential for denaturation, as compared to conventional materials currently being used to contain protein-containing solutions. These efforts were directed to PEO because of its apparent high effectiveness as a protein-compatible material. This protein compatibility is believed to be attributable to stearic stabilization effects of PEO, its unique solution properties, and its molecular conformation in aqueous solution.

Prior to the present invention, however, PEO and other water-soluble polymers could not be used in direct contact with protein-water solutions, as such polymers were deemed soluble in aqueous solutions. Thus, research efforts have been directed to methods of providing water-soluble polymer-type protein compatibility in polymers which will contact protein-containing water solutions. The major objective in these efforts was to prevent the solubility of the water-soluble polymer coating of the matrix polymer back into the aqueous protein solution.

PEO has been chemically bonded through graft copolymerization onto polyvinylchloride, styrene-butadiene-styrene, and many other substrates. Surface grafting and solvent swelling are relatively complex manufacturing processes requiring multiple treatment steps. One of the most difficult of these steps is the removal of the solvent or residual reactive ingredients. Such methods or other modification procedures are expensive, however, and thus not the most cost effective method of immobilizing PEO molecules on polymeric surfaces.

Relevant United States patents include U.S. Pat. Nos. 3,222,314, 3,425,981, 3,426,107, 3,524,905, 3,549,727, 3,645,939, 3,789,085, 4,048,131, 4,228,250, 4,327,009, 4,337,188, 4,362,844, 4,412,025, 4,415,691, 4,464,438, 4,500,677, 4,522,967, 4,600,404, 4,600,746, 4,681,526, 4,701,360, 4,768,376, 4,789,575, 4,802,943, 4,859,513, 4,880,701, 4,883,699, 4,888,222, 4,920,158, 4,948,640, 4,981,739, 4,983,431, 4,988,546, 5,045,594, 5,013,769, 5,023,036 and RE 33,376.

SUMMARY OF THE INVENTION

The invention is a protein-compatible polymer blend made from a water-soluble polymer and a matrix polymer which provides a stable hydrophilic surface. The glass transition temperature of either the water-soluble polymer or the matrix polymer must be greater than the application temperature, i.e., the highest temperature at which the product made from the polymer blend will be exposed during distribution, storage or usage.

The water-soluble polymer is selected from the group including poly(ethylene oxide), poly(ethyl oxazoline), polyvinyl alcohol, poly(acrylamide), poly(vinyl pyrrolidone), and poly(acrylic acid). The matrix polymer is selected from the group including ethylene vinyl acetate, polyolefin, polyvinylchloride, polystyrene, polystyrene-butadiene copolymer, polycarbonate, polyacrylate, polyamide and copolymers thereof, polyurethane, polyester and copolymers thereof.

These protein-compatible polymeric materials can be made by blending a water-soluble polymer or polymers containing segments of water-soluble polymers with a matrix polymer. For example, the blended polymers may be heated in a conventional extruder, and the extrudate removed. This extrudate is pelletized, i.e., cut into small pellets. The pellets are then, in turn, fed into the extruder, and a polymeric film extrudate is manufactured during the subsequent extrusion. This film may be used to fabricate containers for protein-containing liquids or protein solutions. This film may also be laminated to various substrates, and the film-substrate composite used to fabricate containers for protein-containing liquids or protein solutions.

The inventors have found that two of the water-soluble polymers, poly(vinyl alcohol) and poly(ethylene oxide), are quite versatile and preferred, working well with most matrix polymers. The preferred matrix polymers include ethylene vinyl acetate copolymer, polyolefins, polyvinylchloride.

The materials of the present invention may be used at two or more widely differing temperatures. For example, a protein solution container made with the material of the present invention may be stored over an extended period of time at −20° C., maintained at a refrigerated temperature range of 2–8° C., thawed over a relatively short time, and used at ambient temperatures. In this instance, the application temperature would be the ambient temperature, as this is the highest temperature to which the container is exposed during distribution, storage and usage of the container.

The inventors have also found that the selection of suitable water-soluble polymers and matrix polymers depends upon the relative glass transition temperatures. Where the glass transition temperature of the water-soluble polymer is higher than the application temperature, the glass transition temperature of the matrix polymer is irrelevant. When the glass transition temperature of the water-soluble polymer is low, however, the glass transition temperature of the matrix polymer must be higher than both the glass transition temperature of the water-soluble polymer and the temperature at which the resulting polymer will be used, i.e., the application temperature.

It is also desirable that the viscosity of the matrix polymer exceed that of the water-soluble polymer at the extrusion temperature. In this way, the water-soluble polymer will have a greater tendency to spread evenly over and coat the surface of the matrix polymer substrate.

An object of the invention is a novel material that may be made in a number of ways, and which adsorbs significantly less protein from protein-containing solutions with which that material is in contact.

DETAILED DESCRIPTION OF THE PREFERRED EMBODIMENT

The invention is a protein-compatible polymer which can be made in polymeric film or sheet form, or in any other suitable form. In connection with the description of the preferred embodiment, the manufacture of the polymeric film or sheet form will be discussed.

The protein-compatible polymer blend is manufactured from two components. The first component is a water-soluble polymer, or other polymers containing segments of a water-soluble polymer. Examples of preferred water-soluble polymers include poly(ethylene oxide), poly(ethyl oxazoline), poly(vinyl alcohol) (PVOH), poly(acryl amide), poly(vinyl pyrrolidone), and poly(acrylic acid).

The second component of the protein-compatible polymer blend is a so-called matrix polymer. The preferred matrix polymers are selected from the group including polyolefins; ethylene vinyl acetate copolymer; polyurethane; polyvinylchloride, polystyrene, polystyrene-butadiene copolymer, polycarbonate, polyacrylate, polyamide and copolymers thereof, polyurethane, and polyester and copolymers thereof.

Typically, the polymer material made from this polymer blend may be used for a solution container, or for the liner of a solution container made of both a substrate and the polymeric material. This solution container may be used anywhere within a predetermined range of temperatures. The key to the present invention resides in the discovery that a protein-compatible polymer can be made by blending a water-soluble polymer and a matrix polymer where the glass transition temperature of either the water-soluble polymer or the matrix polymer is greater than the application temperature. The blend may then optionally be subjected to shear conditions.

To avoid the undesirability of prior art processes or their products, the present protein-compatible polymer is made by a melt-blending process. Particularly, a small amount of a "protein friendly" polymer is added to a substrate polymer. These protein friendly polymers are all water-soluble polymers, and are added in either powder or pellet form to the substrate or matrix polymer, which is also in powder or pellet form. These components are then tumble-blended until a uniform composition is obtained.

The resulting uniform composition is placed into a compounding single or twin screw extruder. The twin screw extruder is at a temperature higher than the melting temperature of the uniform composition, but lower than the temperature at which that composition would degrade. As an example of an appropriate temperature, the temperature of the extruder for a blend of polyvinyl alcohol (water-soluble polymer) and ethylene vinyl acetate copolymer (matrix polymer) is 380° F.

To ensure that the water-soluble polymer modifier (WSP) will be securely bound to the matrix polymer (MP) on the surface during long-term contact with the aqueous solution, the materials also need to satisfy the glass transition temperature requirements. A material having a higher glass transition temperature than the application temperature will have little molecular mobility. A high glass transition temperature for the water-soluble polymer causes that polymer to "freeze" onto the matrix polymer surface due to its own low mobility. A high glass transition temperature for the matrix polymer "freezes" the water-soluble polymer, preventing it from moving into the aqueous solution. Thus, when the glass transition temperature of either the water-soluble polymer or matrix polymer exceeds the application temperature, the water-soluble polymer will be locked onto the material surface.

To achieve a water-soluble "rich" surface, it is desirable to have shear in the manufacturing of the final product. Under such circumstances, the low viscosity additives or surface modifiers (i.e., the water-soluble polymers) will tend to move onto the surface of the matrix polymer substrate through shear. These conditions can best be created by extrusion or injection molding processes. Thus, in the present invention, a standard monolayer film extrusion procedure using a single screw extruder is preferably used to extrude the blend into a monolayer film. Alternatively, the film of the present invention may be coextruded with another substrate material. The protein-compatible biomaterial or film of the present invention serves as a so-called "skin layer," and is the layer which contacts the protein-containing liquid or protein solution. Shear is desirable, as it is believed to increase the drive of the water-soluble polymer to the surface of the matrix polymer. Shear also lowers the amount of water-soluble polymer that must be added to the matrix polymer.

Notwithstanding the desirability of shear processes in the manufacture of the present invention, other processes may be used. These processes include blow molding, lamination and co-injection.

Table 1 in Example 1, and all of the additional Tables, list results of testing on several polymer blends in accordance with the invention. The second and third columns list contact angles in degrees of the manufactured polymer film or sheets, both initially upon removal from the extruders (after 0 hours) and after immersion in water for 55 or more hours. Contact angle is a measure of the wettability of the surface. Water placed on the surface of a sheet having a 0° contact angle will become flattened or disperse on the surface. In contrast, a sheet having a 180° contact angle is completely "nonwettable." Water placed on the surface of a sheet having a 180° contact angle will bead up into distinct droplets.

The measurement of contact angle at 0 hours was the first of as many as four screening steps used to determine the surface properties of a manufactured film. The contact angle of a film sample in water (Aldrich HPLC grade) was measured using a Wilhelmy Plate tensiometric method with a Cahn Electrobalance for force measurement and a linear voltage displacement transducer (LVDT). Dynamic advancing and receding contact angles were calculated from the force-depth curves.

For the purposes of the present invention, contact angle should be as close to 0° as possible. A low contact angle is a preliminary, although not perfect, indicator of surface coverage. Surface coverage will provide an indication of a film's tendency to adsorb or not adsorb protein. In general, a low contact angle indicates a better surface coverage and, thus, a surface's increased tendency to adsorb water. The use of contact angle is especially applicable for optimizing the ratio of two blended components. In this case, a lower contact angle indicates greater surface coverage of the water-soluble polymer upon the matrix polymer.

The second of the four screening steps measured protein adsorption by a modified Micro-Bicinchoninic Acid (BCA) assay (Pierce Chemicals). Containers were made from the polymer film to be tested. These containers were filled with solutions having predetermined protein concentrations. The containers were then sealed, and the containers and protein solutions were allowed to reach equilibrium over at least the next 18 hours. The containers were then opened, drained of their contents, and rinsed with distilled water for several minutes to remove loosely bound protein. Triton X-100 reagent from Sigma Chemical and the BCA reagent were added to these emptied containers. The residual air in the containers was then removed and the containers resealed. The reagent-containing bags were placed in a 60° C. water bath for 1 hour. At the same time, previously prepared protein standards with these same reagents were placed in the 60° C. water bath.

After 1 hour, the containers were opened and the contents analyzed by a Hewlett Packard Model 8451A diode array UV-visible Absorption Spectroscope at the 562 nm wavelength, using 1-cm disposable polystyrene cuvettes. Adsorption measurements were converted to concentrations using a calibration curve produced from similarly measured standards. The concentrations were blank corrected and converted to protein surface coverage in micrograms per square centimeter using the known surface area of the container.

Columns 4–6 of Table 1 and the remaining Tables relate to protein adsorption by representative sheets using an immunoglobulin G (IgG) fluorescent marker. IgG was chosen as the primary test protein because it adsorbs at surface concentrations higher than that of the other common proteins tested, such as albumin and insulin. It also serves as a model for the general class of monoclonal antibodies. similarly, as recorded in columns 7–9 of Table 1 and the remaining Tables, protein adsorption was measured for representative sheets using an albumin solution.

The third of the four screening tests is the previously described measurement of contact angle after 55 or more hours. This test established whether the protein-compatible surface characteristics were retained after the film had been in contact with the solution over an extended period. In virtually every case, this latter contact angle dropped, indicating the permanency of the water-soluble polymer-modified surfaces on the matrix polymer substrates.

The results of the fourth and final screening test are shown at column 10 of Table 1 and the remaining Tables, and disclose the Total Organic Carbon (TOC), in parts per million, of leachables, e.g., surface modifier additives, in water, after long-term aqueous storage. In the TOC method, all solution organic leachables were converted to carbon dioxide using thermally promoted acidic persulfate oxidation. The carbon dioxide produced was collected and measured by an infrared detector. The TOC analysis was performed on water stored for various periods of time within containers made of the films being studied. The analysis was performed by a commercially available instrument, the Model OI-700 TOC Analyzer from OI Instruments. The significance of TOC is that it provides a direct measurement of leachables going into the solution. Low TOC results are correlated with stability of the water-soluble polymer in the matrix polymer. By analyzing the combined contact angle and TOC results, one can determine whether the water-soluble polymer is firmly anchored onto the matrix polymer.

As many as three separate protein solutions of differing concentrations were used for each of the two types of protein in the test solutions. These three protein concentrations were 2.5 ppm, 10 ppm and 50 ppm.

Solution protein concentration was determined using a Fluoraldehyde Protein assay from Pierce Chemicals. The fluoraldehyde reagent, o-phthalaldehyde, and mercaptoethanol were added to the protein solution to be quantitated. The o-phthalaldehyde reagent reacts with any primary amine groups present on a protein, and in the presence of mercaptoethanol produces an intense blue fluorescent compound showing a wavelength at 340 nm. The fluorescence measurements were made on a Perkin Elmer Model 650-10S fluorescence Spectrophotometer using 1-cm quartz cells.

In no instance were all of these six solutions tested against all films produced. In the Tables, the only solutions and films tested were those showing an entry for protein adsorption.

Specific methods of the manufacture of a polymer blend film in accordance with the invention are discussed in the following illustrative Examples. In each case, a control film included 0% of the water-soluble polymer. The films in accordance with the invention included water-soluble polymer contents of from 0.1% to 25.0%, and even as high as 50%. The preferred range of water-soluble polymer is 0.1% to 10.0%.

PVA and 99.5% EVA, 1.0% PVA and 99.0% EVA, 2.0% PVA and 98.0% EVA, and 5.0% PVA and 95.0% EVA. As a control, one "blend" comprised 0% PVA and 100% EVA. In fact, this was not a blend, but a polymeric sheet made with pure, extruded EVA.

The films were made by blending the PVA and EVA to a uniform consistency, and then placing the uniform blend into a single screw extruder for pelletization. For a blend having 98% EVA and 2% PVA, the pelletizing conditions in the single screw extruder were as follows: Temperatures, Zone #1, 355° F., Zone #2, 390° F., Zone #3, 395° F.; Die Zone #1, 300° F.; Melt temperature, 378° F.; Pressure, 1100 psig; and Load, 8 amperes.

The resulting thin, rod-like, continuous extrudate was discharged from the extruder and then cooled in a water bath, typically a 2 to 10 meter long water-filled trough. Next, this cooled, hardened extrudate was "pelletized," i.e., cut into small, cylindrical pellets. Each of these pellets typically has a diameter of ½ centimeter and a length of ½ centimeter.

These pellets are used as the feedstock for the extrusion of the thin film sheets of the invention. Particularly, these pellets were placed into a 1½" Killion brand or other suitable single screw extruder and then extruded into a thin mono-layer film.

As may be seen from Table 1, greater amounts of PVA resulted in decreased protein adsorption. Using the 2.5 ppm IgG solution, the control film, i.e., the film having no PVA, adsorbed the greatest amount of protein, 0.25 μg protein per square centimeter of film area. In this instance and particular range, the amount of protein adsorption decreased with each increase in the amount of PVA in the polymer blend, with the 5.0% PVA/95.0% EVA blend film adsorbing a mere 0.02 μg protein per square centimeter of the film.

TABLE 1

Ethylene-Vinyl-Acetate (EVA,UE-648)/Poly(vinyl alcohol) (PVA,13K,89% VOH) Blends

| COMPOSITION | CONTACT ANGLE | | PROTEIN ADSORPTION-IgG | | | PROTEIN ADSORPTION-ALBUMIN | | | TOC,ppm, |
|---|---|---|---|---|---|---|---|---|---|
| | Θ, 0 hr. | Θ, 75 hrs. | 2.5 ppm | 10 ppm | 50 ppm | 2.5 ppm | 10 ppm | 100 ppm | 25° C., 200 hrs., in DDW |
| 0% PVA | 68.2 | 62.5 | 0.25 | 0.30 | 0.45 | 0.10 | 0.18 | 0.20 | 2.70 |
| 0.2% PVA | 60.7 | 52.5 | 0.21 | | | | | | |
| 0.5% PVA | 63.7 | 55.1 | 0.16 | | | | | | |
| 1.0% PVA | 56.8 | 42.7 | 0.10 | | | | | | |
| 2.0% PVA | 46.2 | 40.2 | 0.04 | 0.10 | 0.27 | 0.05 | 0.13 | 0.20 | 3.10 |
| 5.0% PVA | 33.6 | 40.2 | 0.02 | 0.09 | 0.18 | 0.03 | 0.11 | 0.18 | 6.00 |

EXAMPLE 1

Poly(vinyl alcohol) (PVA), having an approximate glass transition temperature ($T_g$) of 85° C., was used as the water-soluble polymer, and ethylene vinyl acetate (EVA) (approximate $T_g$ of −20° C.) was used as the matrix polymer. The polyvinyl alcohol used has a molecular weight of approximately 13,000 to 23,000 and is available from Aldrich Chemical. The ethylene vinyl acetate was obtained from Quantum Chemical as Catalog No. UE-648. This particular EVA has an 18% vinyl acetate content and an 82% ethylene content.

The PVA and EVA were blended in the following proportions, by weight: 0.2% PVA and 99.8% EVA, 0.5%

EXAMPLE 2

Poly(vinyl alcohol) (PVA) (approximate $T_g$ of 85° C.), as the water-soluble polymer, and polypropylene (PP) (approximate $T_g$ of 0° C.), as the matrix polymer, were blended in an amount of 5% PVA and 95% PP. The polyvinyl alcohol used has a molecular weight of approximately 13,000 to 23,000 and is available from Aldrich Chemical. The polypropylene was obtained from Rexene Corp. as Catalog No. 23M2C. As a control, a composition of 0% PVA and 100% PP was prepared. Both of these compositions were blended and pelletized, and then extruded into a film. The contact angle of the 0% PVA film at 0 hours was 87, whereas the contact angle of the 5% PVA/95% PP film was 38.8. The lower contact angle for the 5% PVA/95% PP blend gave a preliminary indication that the blend should exhibit increased resistance to protein adsorption.

This preliminary indication was confirmed in protein adsorption testing using an immunoglobulin G (IgG) protein composition at 2.5 ppm. The 0% PVA composition adsorbed 0.24 μg protein per square centimeter. In contrast, the 5% PVA film adsorbed one-quarter of this amount per unit area, 0.06 μg per square centimeter.

TABLE 2

Polypropylene(PP)/Poly(vinyl alcohol)(13K, 89% VOH) Blends

| COMPOSITION | CONTACT ANGLE | | PROTEIN ADSORPTION-IgG |
|---|---|---|---|
| | θ, 0 hr. | θ, 100 hrs. | 2.5 ppm |
| 0% PVA | 87.0 | 80.1 | 0.24 |
| 5% PVA | 38.8 | 0 | 0.06 |

EXAMPLE 3

Ethylene vinyl acetate (EVA) (approximate $T_g$ of −20° C.), as the water-soluble polymer, and poly(ethyl oxazoline) (PEOX) (approximate $T_g$ of 53° C.) of various molecular weights, as the matrix polymer, were blended in various relative amounts. The poly(ethyl oxazoline) in the higher and lower molecular weights were obtained from Dow Chemical as Catalog Nos. PEOX500 and PEOX50, respectively. The formulations comprised, by weight, a blend of 5% PEOX50 and 95% ethylene vinyl acetate, and a blend of 5% PEOX500 and 95% EVA. As a control, a pure EVA film (100% EVA, 0% PEOX) was also prepared.

The films were made by first blending the EVA and PEOX, and then placing the uniform blend into a single screw extruder for pelletization. The pelletizing condition for these blends were as follows: Temperatures, Zone #1, 265° F., Zone #2, 285° F., Zone #3, 285° F.; Die Zone #1, 275° F.; Melt temperature, 295° F.; Pressure, 1400 psig; and Load, 12 amperes.

As can be seen by Table 3, the contact angle at both 0 and 75 hours for PEOX500/EVA blend was far lower than the contact angle of the pure EVA film. This tends to indicate that the 5% PEOX500/95% EVA film would have superior protein-compatible properties to the control, pure EVA film.

These indications were confirmed by testing for protein adsorption using the 2.5 ppm immunoglobulin G solution. The 0% PEOX composition adsorbed 0.25 μg protein per square centimeter, whereas the high molecular weight 5% PEOX/95% EVA film adsorbed 0.04 μg protein per square centimeter. Even PEOX50/EVA film exhibited significantly improved protein compatibility over the control, adsorbing only 0.11 μg protein per square centimeter.

In addition, Table 3 indicates TOC in ppm from a film made from PEOX and EVA. A relatively low TOC results from the EVA/PEOX film, indicating that low amounts of the water-soluble polymer are leaching into the solution. This low leaching proves the stability of the water-soluble polymer-modified surfaces during long-term solution contact.

TABLE 3

EVA(UE-648)/Poly(ethyl oxazoline)(PEOX) Blends

| COMPOSITION | CONTACT ANGLE | | PROTEIN ADSORPTION-IgG | TOC,ppm, 25° C., 200 hrs., in DDW |
|---|---|---|---|---|
| | θ, 0 hr. | θ, 75 hrs. | 2.5 ppm | |
| 0% PEOX | 65.0 | 62.5 | 0.25 | 2.7 |
| 5% PEOX50 | | | 0.11 | 3.1 |
| 5% PEOX500 | 30.0 | 7.8 | 0.04 | 3.8 |

EXAMPLE 4

Two different molecular weights of poly(vinyl pyrrolidone) (PNVP) (approximate $T_g$ of 180° C.), as the water-soluble polymer, and ethylene vinyl acetate (EVA) (approximate $T_g$ of −20° C.), as the matrix polymer, were blended. The ethylene vinyl acetate was obtained from Quantum Chemicals as Catalog No. UE-648. The EVA had an 18% vinyl acetate content and an 82% ethylene content. The two PNVP materials with different molecular weight were obtained from Aldrich Chemical.

The formulated blends comprised, by weight, 5% PNVP, having a molecular weight of 40,000, and 95% EVA; 5% PNVP, having a molecular weight of 24,000, and 95% EVA; and a control having 0% PNVP and 100% EVA. In fact, this control was not a blend, but a polymeric sheet made with pure EVA.

The films were made by blending the PNVP and EVA into a uniform composition, and then placing the composition into an extruder for pelletization. The pellets resulting from pelletization were placed into a single extruder, and extruded into a sheet or film. For example, for a blend containing 95% EVA and 5% PNVP (40K molecular weight), the single screw extrusion conditions were as follows: Temperatures, Zone #1, 380° F., Zone #2, 395° F., Zone #3, 400° F.; Die Zone #1, 380° F.; Melt temperature, 389° F.; Pressure, 3800 psig; and Load, 10 amperes.

The results of Table 4 show that PNVP/EVA blends produce films having superior protein compatibility or resistance as compared to pure EVA films.

TABLE 4

EVA(UE-648)/Poly(vinyl pyrrolidone)(PNVP) Blends

| COMPOSITION | CONTACT ANGLE | | PROTEIN ADSORPTION-IgG |
|---|---|---|---|
| | θ, 0 hr. | θ, 200 hrs. | 2.5 ppm |
| 0% PNVP | 65.0 | 58.5 | 0.25 |
| 5% PNVP40K | 32.3 | 0 | 0.1 |
| 5% PNVP24K | 42.8 | 15.7 | 0.15 |

EXAMPLE 5

Poly(ethylene oxide) (PEO) (approximate $T_g$ of −67° C.) having a molecular weight of 100,000, as the water-soluble polymer, and styrene-butadiene resin (SBR) (approximate $T_g$ of 95° C.), as the matrix polymer, were blended in various relative amounts. The styrene butadiene resin was obtained from Phillips as Catalog No. KR-03. The PEO was obtained from Aldrich Chemical. The blends comprised, by weight, 5% PEO and 95% SBR, and a control having 0% PEO and 100% SBR.

Films were made by blending the PEO and SBR, and then placing the uniform blend in a twin screw extruder for pelletization. The extruder pelletization conditions were as follows: Temperatures, Zone #1, 190° F., Zone #2, 360° F., Zone #3, 390° F., Zone #4, 400° F., Zone #5, 400° F.; Die Zone #1, 400° F.; Pressure, 1100 psig; and Load, 42 amperes.

The resulting thin continuous extrudate is cooled, hardened and pelletized. The resulting pellets serve as the feed for a film extrusion process which occurs under the following conditions: Temperatures, Zone #1, 200° F., Zone #2, 350° F., Zone #3, 370° F., Zone #4, 380° F., Zone #5, 390° F.; Die Zone #1, 380° F.; Pressure, 660 psig; and Load, 20 amperes.

As may be seen from Table 5, the 5% PEO/95% SBR blend showed markedly improved protein compatibility or resistance. Particularly, at a protein solution concentration of 2.5 ppm, the 0% PEO/100% SBR blend adsorbed 0.21 μg protein per square centimeter. In contrast, the 5% PEO/95% SBR blend film adsorbed only 0.03 μg protein per square centimeter.

TABLE 5

Styrene-Butadiene Resin(KR-03)/Poly(ethylene oxide)(PEO) Blends

| COMPOSITION | CONTACT ANGLE | | PROTEIN ADSORPTION-IgG |
|---|---|---|---|
| | θ,0 hr. | θ, 170 hrs. | 2.5 ppm |
| 0% PEO | 92.5 | 70.8 | 0.21 |
| 5% PEO100K | 69.8 | 44.6 | 0.03 |

EXAMPLE 6

Poly(ethylene oxides) (PEO) (approximate $T_g$ of −67° C.) having two different molecular weights were used as the water-soluble polymer with poly(methyl methacrylate) (PMMA) (approximate $T_g$ of 100° C.) as the matrix polymer. The PMMA was obtained from ICI Arylic Inc. as Catalog No. CP-82. Both kinds of PEO, having molecular weights of 100,000 and 600,000, respectively, were obtained from Aldrich Chemical.

The blends formulated comprised, by weight, 5% PEO (MW=100K) and 95% PMMA, 5% PEO (MW=600K) and 95% PMMA, and a control having 0% PEO and 100% PMMA. This latter composition is not a blend, but rather a polymeric sheet made with pure PMMA.

The films were made by blending the PEO and PMMA, and then placing the uniform blend into an extruder for pelletization. After pelletization, the pellets were placed into a film extruder and extruded into a thin film. The extrusion conditions were as follows: Temperatures, Zone #1, 200° F., Zone #2, 370° F., Zone #3, 380° F., Zone #4, 400° F., Zone #5, 410° F.; Pressure, 1100 psig; and Load, 36 amperes.

From a review of Table 6, it appears that the protein compatibility of a film made with a PMMA/PEO blend increased with increasing PEO content and increasing PEO molecular weight.

TABLE 6

Polyacrylate(Poly(methyl methacrylate), PMMA, CP-82)/PEO Blends

| COMPOSITION | CONTACT ANGLE | | PROTEIN ADSORPTION-IgG |
|---|---|---|---|
| | θ, 0 hr. | θ, 170 hrs. | 2.5 ppm |
| 0% PEO | 58.1 | 33.2 | 0.09 |
| 5% PEO100K | 51.4 | 43.8 | 0.06 |
| 5% PEO600K | 45.8 | 45.8 | 0.04 |

EXAMPLE 7

Poly(ethylene oxide) (PEO) (approximate $T_g$ of −67° C.), as the water-soluble polymer, and polyester (PETG) (approximate $T_g$ of 81° C.), as the matrix polymer, were blended in various relative amounts. The polyester was obtained from Eastman Chemical as Catalog No. 6763, and the 600,000 molecular weight PEO was obtained from Aldrich Chemical. The formulated blends comprised, by weight, 5% PEO and 95% polyester. As a control, one blend comprised 0% PEO and 100% PETG.

The films were made by blending the PEO and PETG, and then placing the uniform blend in a twin screw extruder. The pelletizing conditions for these PEO/PETG blends were as follows: Temperatures, Zone #1, 200° F., Zone #2, 360° F., Zone #3, 400° F., Zone #4, 410° F., Zone #5, 420° F.; Die Zone #1, 410° F.; Pressure, 850 psig; and Load, 45 amperes.

The pellets from this pelletization were used as the feed for an extruder. The conditions of the twin screw extruder were as follows: Temperatures, Zone #1, 220° F., Zone #2, 380° F., Zone #3, 400° F., Zone #4, 420° F., Zone #5, 430° F.; Pressure, 1200 psig; and Load, 42 amperes.

Table 7 shows markedly improved protein compatibility for the 5% PEO blend as compared to the pure polyester film.

TABLE 7

Polyester(PETG)/PEO Blends

| COMPOSITION | CONTACT ANGLE | | PROTEIN ADSORPTION-IgG | TOC,ppm, 25° C., 200 hrs., in DDW |
|---|---|---|---|---|
| | θ, 0 hr. | θ, 170 hrs. | 2.5 ppm | |
| 0% PEO | 50.0 | 34.1 | 0.24 | 0.89 |
| 5% PEO600K | 47.9 | 42.2 | 0.07 | 8.39 |

EXAMPLE 8

Poly(ethylene oxide) (PEO) (approximate $T_g$ of −67° C.), as the water-soluble polymer, and a polyamide copolymer (nylon 6,6-nylon 6,10) (XE 3303) (approximate $T_g$ of 50° C.), as the matrix polymer, were blended in various relative amounts. The polyamide copolymer (XE 3303) was obtained from EMS-America Grilon, Inc., as Catalog No. XE 3303. 2% PEO having a molecular weight of 100,000 was blended with 98% XE 3303.

The compounding or pelletizing conditions were as follows: Temperatures, Zone #1, 385° F., Zone #2, 410° F., Zone #3, 430° F.; Die Zone #1, 420° F.; Melt temperature, 436° F.; Pressure, 1,000 psig; and Load, 13 amperes.

The extrusion conditions in the single screw extruder were as follows: Temperatures, Zone #1, 380° F., Zone #2, 390° F., Zone #3, 400° F.; Die Zone #1, 410° F.; Die Zone

2, 400° F.; Melt temperature, 390° F.; Pressure, 2000 psig; and Load, 7 amperes.

As can be seen from Table 8, the 2% PEO film exhibited protein adsorption of 0.12 μg protein per square centimeter when contacted with the 2.5 μm IgG protein solution. In contrast, the control film, made from pure polyamide copolymer and 0% PEO, adsorbs 0.22 μg protein per square centimeter.

TABLE 8

Polyamide Copolymer(Nylon6,6-Nylon6,10, XE 3303)/PEO Blends

| COMPOSITION | CONTACT ANGLE | | PROTEIN ADSORPTION-IgG |
|---|---|---|---|
| | θ, 0 hr. | θ, 55 hrs. | 2.5 ppm |
| 0% PEO | 34.7 | 22.8 | 0.22 |
| 2% PEO100K | 27.3 | 0 | 0.12 |

EXAMPLE 9

Poly(ethylene oxide) (PEO) (approximate $T_g$ of −67° C.), as the water-soluble polymer, and a polyamide (nylon 12) (approximate $T_g$ of 50° C.), as the matrix polymer, were blended in various relative amounts. The polyamide was obtained from EMS-America Grilon, Inc., as Catalog No. L-16. As shown in Table 9, 5% PEO having a molecular weight of 100,000 was blended with 95% XE 3303.

The compounding or pelletizing conditions were as follows: Temperatures, Zone #1, 385° F., Zone #2, 410° F., Zone #3, 430° F.; Die Zone #1, 420° F.; Melt temperature, 436° F.; Pressure, 1,000 psig; and Load, 13 amperes.

The extrusion conditions in the single screw extruder were as follows: Temperatures, Zone #1, 380° F., Zone #2, 390° F., Zone #3, 400° F; Die Zone #1, 410° F.; Die Zone #2, 400° F.; Melt temperature, 390° F.; Pressure, 2000 psig; and Load, 7 amperes.

As can be seen from Table 9, the 5% PEO film exhibited protein adsorption of 0.12 μg protein per square centimeter when contacted with the 2.5 ppm IgG protein solution. In contrast, the control film, made from pure polyamide and 0% PEO, adsorbs 0.22 μg protein per square centimeter.

TABLE 9

Polyamide Copolymer(Nylon 12, L-16, EMS)/PEO Blends

| COMPOSITION | CONTACT ANGLE | | PROTEIN ADSORPTION-IgG | TOC,ppm, 25° C., 200 hrs., in DDW |
|---|---|---|---|---|
| | θ, 0 hr. | θ, 55 hrs. | 2.5 ppm | |
| 0% PEO | 55.0 | 18.0 | 0.31 | 1.34 |
| 5% PEO100K | 39.0 | 31.5 | 0.12 | 2.06 |

EXAMPLE 10

As shown in Table 10a, poly(ethylene oxide) (approximate $T_g$ of −67° C.), as the water-soluble polymer, and a polycarbonate (approximate $T_g$ of 143° C.), as the matrix polymer, were blended in various relative amounts. Particularly, these blends comprised, by weight, 5% of a poly(ethylene oxide) having a molecular weight of 100,000, and 95% of a polycarbonate. Poly(ethyl oxazoline) (PEOX50) (approximate $T_g$ of 53° C.), as the water-soluble polymer and a polycarbonate (approximate $T_g$ of 143° C.), as the matrix polymer, were blended in various relative amounts. Particularly, these blends comprised, by weight, 10% and 30% of a PEOX50, and 90% and 70% of a polycarbonate, respectively; and, as a control, one "blend" comprised of 0% water-soluble polymer and 100% of polycarbonate.

As shown in Table 10b, poly(ethyl oxazoline) (PEOX50) (approximate $T_g$ of 53° C.), as the water-soluble polymer, and a polyamide copolymer (EMS, XE 3303) (approximate $T_g$ of 50° C.), as the matrix polymer, were blended in various relative amounts. Particularly, these blends comprised, by weight, 10% and 30% of a PEOX50, and 90% and 70% of a polyamide copolymer respectively; and, as a control, one "blend" comprised of 0% water-soluble polymer and 100% of polyamide copolymer.

As shown in Table 10c, poly(ethylene oxide) (approximate $T_g$ of −67° C.), as the water-soluble polymer, and a polyamide (EMS, L-16) (approximate $T_g$ of 50° C.), as the matrix polymer, were blended in various relative amounts. Particularly, these blends comprised, by weight, 5% and 7% of a poly(ethylene oxide) having a molecular weight of 100,000, and 95% and 93% of a polyamide, respectively. Poly(ethyl oxazoline) (PEOX50) (approximate $T_g$ of 53° C.), as the water-soluble polymer, and a polyamide (EMS, L-16) (approximate $T_g$ of 50° C.), as the matrix polymer, were blended in various relative amounts. Particularly, these blends comprised, by weight, 10%, 30% and 50% of a PEOX50, and 90%, 70% and 50% of a polycarbonate, respectively; and, as a control, one "blend" comprised of 0% water-soluble polymer and 100% of polyamide.

Extruded films were not made in this Example. Rather, blend samples were prepared by first mixing the ingredients in a Brabender Electronic Plasticoder Torque Rheometer, Model EPL-V5501, at about 225° C. and 75 rpm for five minutes under nitrogen purge.

The mixed blend from the Brabender was then compression-molded using a hot press at 220 to 235° C. for about 4 minutes, followed by a fast cooling to room temperature.

The molded sheet is then cut into small pieces for contact angle measurement.

The polycarbonate was obtained from Mobay as product Makrolon RX-2530. The PEO, whether having a molecular weight of 100,000, was obtained from Aldrich Chemical. Polyamide copolymer (XE 3303) was obtained from EMS-America Grilon, Inc., as Catalog No. XE 3303. Polyamide (Nylon 12) was obtained from EMS-America Grilon, Inc., as Catalog No. L-16. PEOX was obtained from Dow Chemical as Catalog No. PEOX50.

As can be seen from Tables 10a, 10b and 10c, greater amounts of PEO and PEOX reduced the contact angle of the films manufactured. This phenomenon was especially evident after extended film immersion periods in water. As indicated above, a lesser contact angle can be correlated with decreased protein adsorption.

TABLE 10a

Polycarbonate/PEO Blends

| COMPOSITION | CONTACT ANGLE | |
|---|---|---|
| | θ, 0 hr. | θ, 100 hrs. |
| 0% WSP | 63.7 | 49.9 |
| 5% PEO100K | 49.2 | 41.4 |

TABLE 10a-continued

Polycarbonate/PEO Blends

| | CONTACT ANGLE | |
|---|---|---|
| COMPOSITION | θ, 0 hr. | θ, 100 hrs. |
| 10% PEOX50 | 39.4 | 11.7 |
| 30% PEOX50 | 35.9 | 0 |

TABLE 10b

Nylon Copolymer(EMS, XE 3303)/Water Soluble Polymer(WSP) Blends

| | CONTACT ANGLE | |
|---|---|---|
| COMPOSITION | θ, 0 hr. | θ, 55 hrs. |
| 0% WSP | 34.7 | 22.8 |
| 10% PEOX50 | 38.0 | 7(140 hrs.) |
| 30% PEOX50 | 38.0 | 0(140 hrs.) |

TABLE 10c

Nylon 12(EMS, L16)/Water Soluble Polymer (WSP) Blends

| | CONTACT ANGLE | |
|---|---|---|
| COMPOSITION | θ, 0 hr. | θ, 385 hrs. |
| 0% WSP | 60.3 | 49.6 |
| 5% PEO100K | 61.6 | 35.0 |
| 7% PEO100K | 54.7 | 24.8 |
| 10% PEOX50 | 33.6 | 20.4(120 hrs) |
| 30% PEOX50 | 30.4 | 25.4(120 hrs) |
| 50% PEOX50 | 31.4 | 16.4(120 hrs) |

While the specific embodiments have been illustrated and described, numerous modifications come to mind without markedly departing from the spirit of the invention. The scope of protection is, thus, only intended to be limited by the scope of the accompanying Claims.

What we claim is:

1. A protein-compatible film product made from a polymer blend, said product being made by the extrusion shearing of said polymer blend, said polymer blend comprising:
   a. a water-soluble polymer selected from the group consisting of poly(ethylene oxide), poly(vinyl alcohol), poly(ethyl oxazoline), poly(acryl amide), and poly(vinyl pyrrolidone); and,
   b. a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;
   wherein the glass transition temperature of at least one of said water-soluble polymer or matrix polymer is greater than the application temperature, which is the highest temperature at which the product will be exposed during distribution, storage, or usage, and while in contact with a protein-containing solution; and
   wherein protein adsorption of the film product is reduced in an amount within the range of from about 16% to about 92% as compared to a protein adsorption of a corresponding second product comprising 100% by weight of the same matrix polymer.

2. A film consisting essentially of a protein-compatible product of claim 1, wherein the amount of said water-soluble polymer in said polymer blend is from 0.1% to 50.0% (wt.).

3. A container for pharmaceuticals consisting essentially of the protein-compatible product of claim 1.

4. A medical device consisting essentially of the protein-compatible product of claim 1.

5. A protein-compatible polymer film, said film being made by the shearing of a polymer blend, said polymer blend comprising:
   a. a water-soluble polymer selected from the group consisting of poly(ethylene oxide), poly(ethyl oxazoline), poly(vinyl alcohol), poly(acryl amide), and poly(vinyl pyrrolidone); and
   b. a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;
   wherein the glass transition temperature of at least one of said water-soluble polymer or said matrix polymer is greater than the application temperature, which is the highest temperature at which the film will be exposed during distribution, storage, or usage, and while in contact with a protein-containing solution; and
   wherein protein adsorption of the polymer blend is reduced in an amount within the range of from about 16% to about 92% as compared to a protein adsorption of a second product comprising 100% by weight of the same matrix polymer.

6. The protein-compatible polymer film of claim 5, wherein the amount of said water-soluble polymer is from 0.1 to 50.0% (wt.).

7. A container for pharmaceuticals consisting essentially of the film of claim 5.

8. A medical device consisting essentially of the film of claim 5.

9. A method of manufacturing a protein compatible film from a polymer blend, comprising the steps of:
   a. thoroughly blending a water-soluble polymer selected from the group consisting of poly(ethylene oxide), poly(vinyl alcohol), poly(ethyl oxazoline), poly(acryl amide), and poly(vinyl pyrrolidone) with a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters into a blend,
   wherein the glass transition temperature of at least one of said water-soluble polymer or matrix polymer is greater than the application temperature, which is the highest temperature at which the film will be exposed during distribution, storage, or usage, and while in contact with a protein-containing solution, and wherein protein adsorption of the polymer blend is reduced in an amount within the range of from about 16% to about 92% as compared to a protein adsorption of a corresponding second product of 100% by weight of the same matrix polymer;
   b. melting said blend; and
   c. exposing said blend to shear conditions such that said water-soluble polymer will move onto the surface of the matrix polymer substrate through shear.

10. The method as set forth in claim 9, wherein said blend is exposed to shear conditions through extrusion or injection molding processes.

11. The method as set forth in claim 10, wherein said extrusion process is a film extrusion process.

12. A container for pharmaceuticals consisting essentially of the protein-compatible polymer blend made by the method of claim 9.

13. A medical device consisting essentially of the protein-compatible polymer blend made by the method of claim 9.

14. A protein-compatible product made from a polymer blend, said polymer blend comprising:
   a. a water-soluble polymer selected from the group consisting of poly(ethylene oxide), poly(vinyl alcohol), poly(ethyl oxazoline), poly(acryl amide), and poly(vinyl pyrrolidone); and
   b. a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;
   wherein the glass transition temperature of at least one of said water-soluble polymer or matrix polymer is greater than the application temperature, which is the highest temperature at which the film will be exposed during distribution, storage, or usage, and while in contact with a protein-containing solution; and
   wherein protein adsorption of the polymer blend is reduced in an amount within the range of from about 16% to about 92% as compared to a protein adsorption of a second product of 100% by weight of the same matrix polymer.

15. A protein-compatible product made from a polymer blend, said polymer blend comprising:
   a. a water-soluble polymer from about 0.2% to about 5.0% by weight, wherein the water-soluble polymer is selected from the group consisting of poly(ethylene oxide), poly(vinyl alcohol), poly(ethyl oxazoline), poly(acryl amide), and poly(vinyl pyrrolidone); and
   b. a matrix polymer from about 95.0% to about 99.8% by weight, wherein the matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;
   wherein protein adsorption of the product is reduced in an amount within the range of from about 16% to about 92% as compared to protein adsorption of a second product comprising 100% by weight of the same matrix polymer.

16. The protein-compatible product of claim 15 wherein the glass transition temperature of at least one of the water-soluble polymer or the matrix polymer of the polymer blend is greater than the application temperature at which the protein-compatible product is being used.

17. A film consisting essentially of the protein-compatible product of claim 15.

18. A container for pharmaceuticals consisting essentially of the protein-compatible product of claim 15.

19. A medical device consisting essentially of the protein-compatible product of claim 15.

20. A protein-compatible product made from a polymer blend, said polymer blend comprising:
   a. a water-soluble polymer from about 0.2% to about 5.0% by weight, wherein the water-soluble polymer is selected from the group consisting of poly(ethylene oxide), poly(vinyl alcohol), poly(ethyl oxazoline), poly(acryl amide), and poly(vinyl pyrrolidone); and
   b. a matrix polymer from about 95.0% to about 99.8% by weight, wherein the matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;
   wherein the contact angle of the product is reduced in an amount within the range of from about 11% to about 51% as compared to the contact angle of a second product comprising 100% by weight of the same matrix polymer.

21. The protein-compatible product of claim 20 wherein the glass transition temperature of at least one of the water-soluble polymer or the matrix polymer of the polymer blend is greater than the application temperature at which the protein-compatible product is being used.

22. A film consisting essentially of the protein-compatible product of claim 20.

23. A container for pharmaceuticals consisting essentially of the protein-compatible product of claim 20.

24. A medical device consisting essentially of the protein-compatible product of claim 20.

25. A protein-compatible film product made from a polymer blend, said product being made by the extrusion shearing of said polymer blend, said polymer blend comprising:
   a. a water-soluble polymer selected from the group consisting of poly(ethylene oxide), poly(vinyl alcohol), poly(ethyl oxazoline), poly(acryl amide), and poly(vinyl pyrrolidone); and,
   b. a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;
   wherein the glass transition temperature of at least one of said water-soluble polymer or matrix polymer is greater than the application temperature, which is the highest temperature at which the product will be exposed during distribution, storage, or usage, and while in contact with a protein-containing solution; and
   wherein protein adsorption of the film product is reduced in an amount of at least about 16% as compared to a protein adsorption of a corresponding second product comprising 100% by weight of the same matrix polymer.

26. A film consisting essentially of a protein-compatible product of claim 25, wherein the amount of said water-soluble polymer in said polymer blend is from 0.1% to 50.0% (wt.).

27. A container for pharmaceuticals consisting essentially of the protein compatible product of claim 25.

28. A medical device consisting essentially of the protein-compatible product of claim 25.

29. A protein-compatible polymer film, said film being made by the shearing of a polymer blend, said polymer blend comprising:
   a. a water-soluble polymer selected from the group consisting of poly(ethylene oxide), poly(ethyl oxazoline), poly(vinyl alcohol), poly(acryl amide), and poly(vinyl pyrrolidone); and
   b. a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;

wherein the glass transition temperature of at least one of said water-soluble polymer or said matrix polymer is greater than the application temperature, which is the highest temperature at which the film will be exposed during distribution, storage, or usage, and while in contact with a protein-containing solution; and wherein protein adsorption of the polymer blend is reduced in an amount of at least about 16% as compared to a protein adsorption of a second product comprising 100% by weight of the same matrix polymer.

30. The film of claim 29 wherein the amount of said water-soluble polymer in said polymer blend is from 0.1% to 50.0% (wt.).

31. A container for pharmaceuticals consisting essentially of the film of claim 29.

32. A medical device consisting essentially of the film of claim 29.

33. A method of manufacturing a protein compatible film from a polymer blend, comprising the steps of:
  a. thoroughly blending a water-soluble polymer selected from the group consisting of poly(ethylene oxide), poly(vinyl alcohol), poly(ethyl oxazoline), poly(acryl amide), and poly(vinyl pyrrolidone) with a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters into a blend,
  wherein the glass transition temperature of at least one of said water-soluble polymer or matrix polymer is greater than the application temperature, which is the highest temperature at which the film will be exposed during distribution, storage, or usage, and while in contact with a protein-containing solution, and wherein protein adsorption of the polymer blend is reduced in an amount of at least about 16% compared to a protein adsorption of a corresponding second product of 100% by weight of the same matrix polymer;
  b. melting said blend; and
  c. exposing said blend to shear conditions such that said water-soluble polymer will move onto the surface of the matrix polymer substrate through shear.

34. A container for pharmaceuticals consisting essentially of the protein compatible polymer made by the method of claim 33.

35. A medical device consisting essentially of the protein compatible polymer made by the method of claim 33.

36. A protein-compatible product made from a polymer blend, said polymer blend comprising:
  a. a water-soluble polymer selected from the group consisting of poly(ethylene oxide), poly(vinyl alcohol), poly(ethyl oxazoline), poly(acryl amide), and poly(vinyl pyrrolidone); and
  b. a matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;

wherein the glass transition temperature of at least one of said water-soluble polymer or matrix polymer is greater than the application temperature, which is the highest temperature at which the film will be exposed during distribution, storage, or usage, and while in contact with a protein-containing solution; and wherein protein adsorption of the polymer blend is reduced in an amount of at least about 16% compared to a protein adsorption of a second product of 100% by weight of the same matrix polymer.

37. A film consisting essentially of a protein-compatible product of claim 36, wherein the amount of said water-soluble polymer in said polymer blend is from 0.1% to 50.0% (wt.).

38. A container for pharmaceuticals consisting essentially of the protein compatible product of claim 36.

39. A medical device consisting essentially of the protein-compatible product of claim 36.

40. A protein-compatible product made from a polymer blend, said polymer blend comprising:
  a. a water-soluble polymer from about 0.2% to about 5.0% by weight, wherein the water-soluble polymer is selected from the group consisting of poly(ethylene oxide), poly(vinyl alcohol), poly(ethyl oxazoline), poly(acryl amide), and poly(vinyl pyrrolidone); and
  b. a matrix polymer from about 95.0% to about 99.8% by weight wherein the matrix polymer selected from the group consisting of ethylene vinyl acetate copolymers, polyolefins, polyvinylchloride, polystyrene polymers and copolymers of polystyrenes, polycarbonate, polyacrylates polyamide polymers and copolymers of polyamides and polyester polymers and copolymers of polyesters;

wherein protein adsorption of the product is reduced in an amount of at least about 16% compared to a protein adsorption of a second product comprising 100% by weight of the same matrix polymer.

41. A container for pharmaceuticals consisting essentially of the protein compatible product of claim 40.

42. A medical device consisting essentially of the protein-compatible product of claim 40.

43. A protein-compatible product made from a polymer blend, said polymer blend comprising:
  a. a water-soluble polymer from about 0.2% to about 5.0% by weight, wherein the water-soluble polymer is selected from the group consisting of poly(ethylene oxide), poly(vinyl alcohol), poly(ethyl oxazoline), poly(acryl amide) and poly(vinyl pyrrolidone); and
  b. a matrix polymer from about 95.0% to about 99.8% by weight wherein the matrix polymer selected from the group consisting of ethylene vinyl acetate copolymers, polyolefins, polyvinylchloride, polystyrene polymers and copolymers of polystyrenes, polycarbonate, polyacrylates, polyamide polymers and copolymers of polyamides, and polyester polymers and copolymers of polyesters;

wherein the contact angle of the product is reduced in an amount of at least about 11% compared to the contact angle of a second product comprising 100% by weight of the same matrix polymer.

44. A container for pharmaceuticals consisting essentially of the protein compatible product of claim 43.

45. A medical device consisting essentially of the protein-compatible product of claim 43.

* * * * *